United States Patent [19]

Koike et al.

[11] Patent Number: 4,772,596

[45] Date of Patent: Sep. 20, 1988

[54] DIHYDROPYRIDINE DERIVATIVES, THEIR PREPARATION AND THEIR USE

[75] Inventors: Hiroyuki Koike; Hiroshi Nishino; Masafumi Yoshimoto, all of Tokyo, Japan

[73] Assignees: Sankyo Company Limited, Tokyo; Ube Industries Limited, Ube, both of Japan

[21] Appl. No.: 105,388

[22] Filed: Oct. 5, 1987

[30] Foreign Application Priority Data

Oct. 9, 1986 [JP] Japan .................. 61-240254

[51] Int. Cl.$^4$ ................ A61K 31/445; A61K 31/455; C07D 401/12

[52] U.S. Cl. .................. 514/210; 514/318; 514/340; 546/194; 546/281; 546/275

[58] Field of Search .............. 546/194, 275, 281; 514/210, 318, 340

[56] References Cited

U.S. PATENT DOCUMENTS

| | | | |
|---|---|---|---|
| 3,775,422 | 11/1973 | Bossert et al. | 546/321 |
| 3,935,223 | 1/1976 | Meyer et al. | 546/310 |
| 4,220,649 | 9/1980 | Kojima et al. | 546/281 |
| 4,448,964 | 5/1984 | Muto et al. | 546/194 |
| 4,565,824 | 1/1986 | Wehinger et al. | 546/321 |
| 4,579,859 | 4/1986 | Ueda et al. | 546/321 |
| 4,603,135 | 7/1986 | Meguro et al. | 546/321 |

FOREIGN PATENT DOCUMENTS

| | | |
|---|---|---|
| 125803 | 11/1984 | European Pat. Off. . |
| 1173862 | 12/1969 | United Kingdom . |
| 1455502 | 11/1976 | United Kingdom . |

OTHER PUBLICATIONS

Arzneim-Forsh., 31, 1173(1981).

*Primary Examiner*—Mary C. Lee
*Assistant Examiner*—Dale A. Bjorkman
*Attorney, Agent, or Firm*—Frishauf, Holtz, Goodman & Woodward

[57] ABSTRACT

2-(Amino or methyl)-6-(methyl or amino)-4-(substituted phenyl)-1,4-dihydropyridine-3,5-dicarboxylic acid esters have a specific class of heterocyclic groups as thealcohol moiety. These compounds have a variety of valuable activities, including antihypertensive and $Ca^{++}$-blocking activities, leading to their use for the treatment of circulatory and coronary disorders. They may be prepared by condensation of appropriate substituted benzylideneacetoacetic acid esters with appropriate amidinoacetic acid esters.

25 Claims, No Drawings

DIHYDROPYRIDINE DERIVATIVES, THEIR PREPARATION AND THEIR USE

BACKGROUND OF THE INVENTION

The present invention relates to a series of new dihydropyridine derivatives, and provides a process for preparing them as well as means for their pharmaceutical use.

Circulatory and coronary disorders are amongst the major causes of death in the industrialized world and, even where they do not result in death, disablement or a severe curtailment of lifestyle may result. Notwithstanding this, the full etiology of such disorders has not been resolved, even though certain factors, notably genetic and dietary factors, have been implicated. There is, therefore, a substantial need for medicines to treat this major problem. In attempting to treat circulatory and coronary disorders, attention has been focused on a variety of different pharmacodynamic activities, and the drugs used in such treatment have a variety of different structures, depending upon the particular pharmacodynamic activity which it it is desired to influence.

Of the many classes of drug proposed for use in such treatment, some compounds have a 4-(substituted phenyl)-1,4-dihydropyridine basic structure and included within such general classes of drug are Nifedipine (which is included amongst the compounds disclosed in British Patent Specification No. 1,173,862) and Nicardipine (which is included amongst the compounds disclosed in British Patent Specification No. 1,455,502). All of these compounds have in common a 4-(nitrophenyl)-2,6-dimethyl-1,4-dihydropyridine-3,5-dicarboxylic acid ester structure.

However, it is believed that the closest prior art to the compounds of the present invention is disclosed in Arzneim.—Forsh., 31, 1173 (1981) and in European Patent Publication No. 125 803. Both of these disclose compounds which are said to have cardiovascular activity, in much the same way as do the compounds of the present invention. However, the compounds of the former prior art differ from those of the present invention in the nature of the ester grouping at the 1,4-dihydropyridine system. The latter prior art, although disclosing compounds some of which have an ester grouping resembling that of the present invention, differ in the overall structure of the compounds and notably in the nature of the groups at the 2- and 6-positions of the dihydropyridine ring.

Other related compounds are disclosed in U.S. patent application Ser. No. 873,946, filed the 13th day of June, 1986, which has been replaced by continuation application Ser. No. 146,713 filed Jan. 21, 1988, but these differ from the compounds of the present invention in that the prior compounds contain a nitrooxy group in their molecular structure, which is not possessed by the compounds of the present invention.

BRIEF SUMMARY OF INVENTION

It is an object of the present invention to provide a series of novel dihydropyridine derivatives having excellent calcium-blocking activity, as well as antihypertensive, antihyperlipemic and vasodilator activities and the ability to inhibit the formation of lipid peroxides.

It is a further object of the invention to provide methods and compositions for using such compounds in the treatment and prophylaxis of circulatory, especially cardiovascular, disorders.

It is a still further object of the invention to provide processes for producing such compounds.

The compounds of the invention are those dihydropyridine derivatives of formula (I):

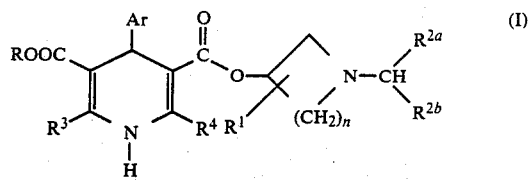

in which:

Ar represents a phenyl group having at least one substituent selected from the group consisting of nitro, $C_1$–$C_4$ haloalkyl, $C_1$–$C_4$ haloalkoxy and cyano groups and halogen atoms;

R represents a $C_1$–$C_{16}$ alkyl group, a $C_3$–$C_6$ cycloalkyl group, a $C_1$–$C_4$ alkyl group having a $C_3$–$C_6$ cycloalkyl substituent, a $C_2$–$C_4$ alkenyl group, a cinnamyl group or a $C_1$–$C_{16}$ alkyl group having at least one substituent selected from the group consisting of hydroxy, $C_1$–$C_4$ alkoxy and $C_1$–$C_4$ alkylthio groups;

$R^1$ represents a hydrogen atom or a $C_1$–$C_3$ alkyl group (and may be a substituent on any of the carbon atoms of the nitrogen-containing heterocyclic group);

$R^{2a}$ and $R^{2b}$ are independently selected from the group consisting of unsubstituted phenyl groups and substituted phenyl groups having at least one substituent selected from the group consisting of $C_1$–$C_4$ alkyl, $C_1$–$C_4$ alkoxy and $C_1$–$C_4$ haloalkyl groups and halogen atoms;

one of $R^3$ and $R^4$ represents a methyl group and the other represents an amino group; and n is an integer from 1 to 3;

and pharmaceutically acceptable acid addition salts thereof.

DETAILED DESCRIPTION OF THE INVENTION

The compounds of the present invention have been found to have various valuable pharmacological activities such as calcium antagonism, antihypertensive and vasodilator activity as well as low toxicity and are thus useful as medicines for the treatment of cardiovascular dysfunctions such as hypertension and angina pectoris.

In the compounds of the invention, Ar represents a phenyl group which has at least one, and preferably only one, nitro, $C_1$–$C_4$ haloalkyl, $C_1$–$C_4$ haloalkoxy or cyano substituent, or at least one, and preferably one or two, halogen substituents.

In particular, we prefer that Ar should represent a phenyl group having a single substituent selected from the group consisting of nitro groups, haloalkyl groups containing one or two carbon atoms (such as the trifluoromethyl or 2,2,2-trifluoroethyl groups), haloalkoxy groups containing one or two carbon atoms (such as the difluoromethoxy group, trifluoromethoxy group or 2,2-difluoroethoxy group) and cyano groups. Alternatively, we prefer that Ar should represent a phenyl group containing one or two halogen atoms (such as the fluorine, chlorine, bromine or iodine atoms. Preferred such groups represented by Ar are the o-nitrophenyl, m-nitrophenyl, p-nitrophenyl, o-chlorophenyl, m- chlorophenyl, p-chlorophenyl, o-cyanophenyl, m-cyanophenyl, o-trifluoromethylphenyl, m-trifluoromethylphenyl, o-difluoromethoxyphenyl, m-difluoromethoxyphenyl, 2,3-dichlorophenyl, 3,4-dichlorophenyl, 3,5-dichlorophenyl and 2,4-dichlorophenyl groups. Of these, we particularly prefer the o-nitrophenyl, m-nitrophenyl, o-chlorophenyl, m-chlorophenyl and 2,3-dichlorophenyl groups.

$R^1$ represents a hydrogen atom or an alkyl group having from 1 to 3 carbon atoms. Examples of such groups include the methyl, ethyl, propyl and isopropyl groups. The hydrogen atom and the methyl group are preferred, and the hydrogen atom is most preferred.

$R^{2a}$ and $R^{2b}$ are the same or different and each represents a phenyl group which may be unsubstituted or have at least one $C_1$-$C_4$ alkyl, $C_1$-$C_4$ alkoxy, $C_1$-$C_4$ haloalkyl or halogen substituent and the two groups represented by $R^{2a}$ and $R^{2b}$ may be the same or different, but they are preferably the same. Where the substituent is an alkyl group, this is preferably a $C_1$-$C_3$ alkyl group, such as a methyl, ethyl, propyl or isopropyl group. Where the substituent is an alkoxy group, this is preferably a $C_1$-$C_3$ alkoxy group, such as methoxy, ethoxy, propoxy or isopropoxy group. Where the substituent is a halogen atom, this is preferably a fluorine, chlorine, bromine or iodine atom. Where the substituent is a haloalkyl group, this is preferably a $C_1$ or $C_2$ haloalkyl group, such as a trifluoromethyl or 2,2,2-trifluoroethyl group, especially a trifluoromethyl group.

Where R represents a straight or branched chain alkyl group containing from one to sixteen carbon atoms, it preferably has from one to ten carbon atoms, and examples include the methyl, ethyl, propyl, isopropyl, butyl, isobutyl, pentyl, hexyl, heptyl, octyl and decyl groups. Such groups may be unsubstituted or may have one or more, and preferably only one substituent, as defined below.

The $C_1$-$C_{16}$ alkyl groups represented by R may be unsubstituted or have at least one substituent selected from the group consisting of hydroxy groups, $C_1$-$C_4$, preferably $C_1$-$C_3$, alkoxy groups (such as the methoxy, ethoxy, propoxy or isopropoxy groups) or $C_1$-$C_4$, preferably $C_1$-$C_3$, alkylthio groups (such as the methylthio, ethylthio, propylthio or isopropylthio groups).

Where R represents a cycloalkyl group containing from three to six carbon atoms, it may be, for example, a cyclopropyl, cyclobutyl, cyclopentyl or cyclohexyl group. Where R represents a $C_1$-$C_4$ alkyl group having a $C_3$-$C_6$ cycloalkyl substituent, this is a cycloalkylalkyl group containing four to eight carbon atoms, and examples include the cyclopropylmethyl, cyclopentylmethyl, cyclohexylmethyl, 2-cyclopropylethyl, 2-cyclopentylethyl and 2-cyclohexylethyl groups. Where R represents a $C_2$-$C_4$ alkenyl group, it is preferably an alkenyl group containing three or four carbon atoms, for example an allyl or 2-butenyl group.

One of $R^3$ and $R^4$ represents a methyl group and the other represents an amino group; thus, the compounds of the present invention may be divided into two classes, as illustrated by formulae (Ia) and (Ib):

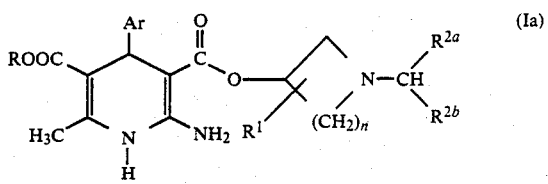

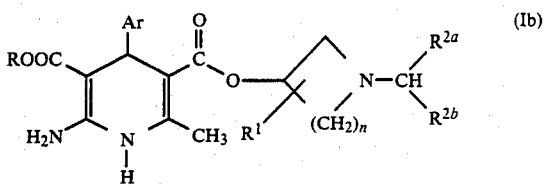

in which Ar, R, $R^1$, $R^{2a}$ and $R^{2b}$ are as defined above; in these formulae, $R^{2a}$ and $R^{2b}$ are preferably the same groups.

Preferred classes of compounds of the present invention are:
(1) Those compounds of formula (I) in which:

Ar represents a phenyl group having a single substituent selected from the group consisting of nitro, $C_1$-$C_2$ haloalkyl, $C_1$-$C_2$ haloalkoxy and cyano groups or one or two substituents selected from the group consisting of halogen atoms;

R represents a $C_1$-$C_{10}$ alkyl group, a $C_3$-$C_6$ cycloalkyl group, a $C_1$-$C_2$ alkyl group having a $C_3$-$C_6$ cycloalkyl substituent, a $C_3$-$C_4$ alkenyl group, a cinnamyl group or a $C_1$-$C_{10}$ alkyl group having at least one substituent selected from the group consisting of hydroxy, $C_1$-$C_3$ alkoxy and $C_1$-$C_3$ alkylthio groups;

$R^1$ represents a hydrogen atom or a $C_1$-$C_3$ alkyl group;

$R^{2a}$ and $R^{2b}$ are independently selected from the group consisting of unsubstituted phenyl groups and substituted phenyl groups having at least one substituent selected from the group consisting of $C_1$-$C_3$ alkyl, $C_1$-$C_3$ alkoxy and trifluoromethyl groups and halogen atoms;

one of $R^3$ and $R^4$ represents a methyl group and the other represents an amino group; and n is an integer from 1 to 3;

and pharmaceutically acceptable acid addition salts thereof. (2) Those compounds defined in (1) above in which $R^{2a}$ and $R^{2b}$ are the same. (3) Those compounds defined in (1) or (2) above in which $R^3$ represents a methyl group and $R^4$ represents an amino group.

More preferred classes of compounds of the present invention are:
(4) Those compounds of formula (I) in which:

Ar represents a phenyl group having a single substituent selected from the group consisting of nitro, trifluoromethyl, difluoromethoxy and cyano groups or having one or two chloro substituents;

R represents a alkyl group (especially one containing from one to six carbon atoms, such as a methyl, ethyl, propyl, isopropyl, butyl, isobutyl, pentyl or hexyl group), an alkoxyalkyl group containing a total of from three to five carbon atoms (such as a 2-methoxyethyl, 2-ethoxyethyl or 2-propoxyethyl group), an alkylthioalkyl group containing a total of three or four carbon atoms (such as a 2-methylthioethyl, 3-methylthiopropyl or 2-ethylthioethyl group), a cycloalkyl group containing five or six carbon atoms (such as a cyclopentyl or cyclohexyl group), a cycloalkylalkyl group containing a total of from four to seven carbon atoms (such as a cyclopropylmethyl, cyclopentylmethyl or cyclohexylmethyl group), an alkenyl group containing three or four carbon atoms (such as an allyl or 2-butenyl group), or a cinnamyl group;

$R^1$ represents a hydrogen atom or a methyl group; and $R^{2a}$ and $R^{2b}$ are the same and each represents a phenyl group or a phenyl group having a single substituent selected from the group consisting of chlorine atoms, fluorine atoms, trifluoromethyl groups, methyl groups and methoxy groups;

and pharmaceutically acceptable acid addition salts thereof. (5) Those compounds defined in (4) above in which $R^3$ represents a methyl group and $R^4$ represents an amino group.

The most preferred classes of compounds of the present invention are:

(6) Those compounds of formula (I) in which:

Ar represents a 2-nitrophenyl group, a 3-nitrophenyl group, a 2-trifluoromethylphenyl group, a 3-trifluoromethylphenyl group, a 2-chlorophenyl group or a 2,3-dichlorophenyl group;

R represents a methyl, ethyl, propyl, isopropyl, butyl, isobutyl, pentyl, hexyl, 2-methoxyethyl, 2-ethoxyethyl, 2-propoxyethyl, 2-methylthioethyl, 3-methylthiopropyl, 2-ethylthioethyl, cyclopentyl, cyclohexyl, cyclopropylmethyl, cyclopentylmethyl, cyclohexylmethyl, allyl, 2-butenyl or a cinnamyl group;

$R^1$ represents a hydrogen atom or a methyl group; and $R^{2a}$ and $R^{2b}$ are the same and each represents a phenyl group or a p-fluorophenyl group;

and pharmaceutically acceptable acid addition salts thereof. (7) Those compounds defined in (6) above in which $R^3$ represents a methyl group and $R^4$ represents an amino group.

The compounds of the invention can form acid addition salts. The nature of such salts is not critical to the present invention, except that, where the salts are to be used for therapeutic purposes, they must be pharmaceutically acceptable, which, as is well understood in the art, means that the salts should not have reduced activity (or unacceptably reduced activity) and should not have increased toxicity (or unacceptably increased toxicity) as compared with the free compound. However, where the salt is to be employed for other purposes, for example as an intermediate in the preparation of other compounds, even this criterion does not apply. A wide variety of acids may be employed to form such salts and representative examples of such acids include: mineral acids, such as hydrochloric acid, hydrobromic acid, hydroiodic acid, phosphoric acid, metaphosphoric acid, nitric acid or sulfuric acid; organic carboxylic acids, such as acetic acid, oxalic acid, tartaric acid, citric acid, benzoic acid, glycolic acid, gluconic acid, glucuronic acid, succinic acid, maleic acid or fumaric acid; and organic sulfonic acids, such as methanesulfonic acid, ethanesulfonic acid, benzenesulfonic acid or p-toluenesulfonic acid. Such acid addition salts may be prepared by conventional methods.

The compounds of formula (I) may contain several asymmetric carbon atoms, and thus can form a variety of optical isomers. The present invention includes both the individual isolated isomers and mixtures thereof.

Examples of specific compounds of the invention are given in the following formulae (I-1) to (I-7), in which the substituents are as defined in the corresponding one of Tables 1 to 7 [i.e. Table 1 relates to formula (I-1), Table 2 relates to formula (I-2) and so on]. The compounds of the invention are hereinafter, where appropriate, identified by the numbers appended to them in these Tables. In the Tables, the following abbreviations are used:

| | |
|---|---|
| All | allyl |
| Bu | butyl |
| iBu | isobutyl |
| Bun | 2-butenyl |
| Cim | cinnamyl |
| Dc | decyl |
| DFM | difluoromethyl |
| Et | ethyl |
| Hp | heptyl |
| Hx | hexyl |
| cHx | cyclohexyl |
| Me | methyl |
| Oc | octyl |
| Ph | phenyl |
| Pn | pentyl |
| cPn | cyclopentyl |
| Pr | propyl |
| cPr | cyclopropyl |
| iPr | isopropyl |
| TFM | trifluoromethyl |

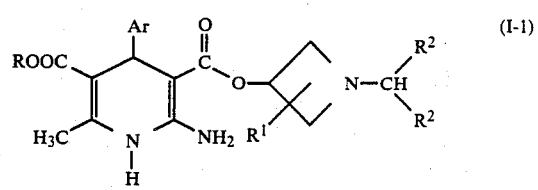

(I-1)

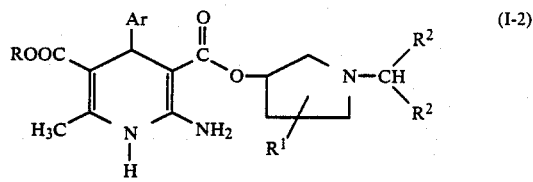

(I-2)

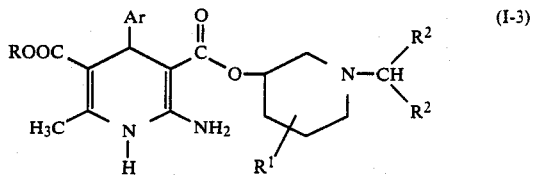

(I-3)

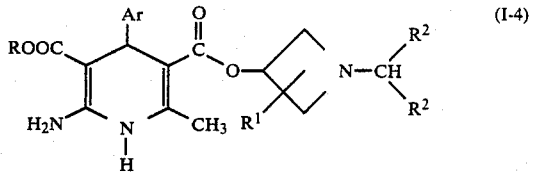

(I-4)

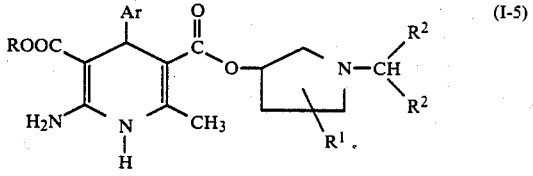

(I-5)

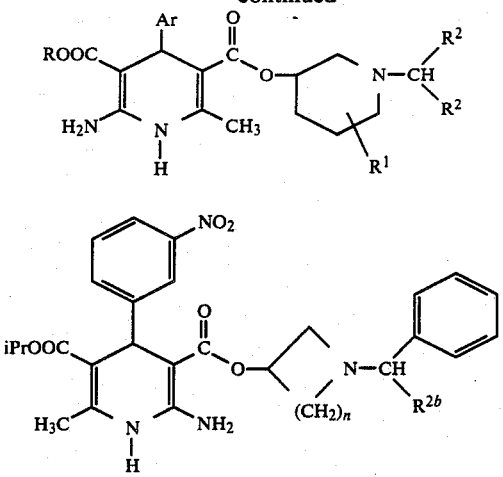

(I-6)

(I-7)

TABLE 1

| Compound No. | Ar | R | R¹ | R² |
|---|---|---|---|---|
| 1-1 | o-NO₂Ph | Me | H | Ph |
| 1-2 | o-NO₂Ph | Et | H | Ph |
| 1-3 | o-NO₂Ph | iPr | H | Ph |
| 1-4 | o-NO₂Ph | Hx | H | Ph |
| 1-5 | o-NO₂Ph | 2-MeOEt | H | Ph |
| 1-6 | o-NO₂Ph | cHx | H | Ph |
| 1-7 | o-NO₂Ph | Cim | H | Ph |
| 1-8 | m-NO₂Ph | Me | H | Ph |
| 1-9 | m-NO₂Ph | Et | H | Ph |
| 1-10 | m-NO₂Ph | Pr | H | Ph |
| 1-11 | m-NO₂Ph | iPr | H | Ph |
| 1-12 | m-NO₂Ph | Bu | H | Ph |
| 1-13 | m-NO₂Ph | iBu | H | Ph |
| 1-14 | m-NO₂Ph | Pn | H | Ph |
| 1-15 | m-NO₂Ph | Hx | H | Ph |
| 1-16 | m-NO₂Ph | HP | H | Ph |
| 1-17 | m-NO₂Ph | Oc | H | Ph |
| 1-18 | m-NO₂Ph | Dc | H | Ph |
| 1-19 | m-NO₂Ph | 6-HOHx | H | Ph |
| 1-20 | m-NO₂Ph | 2-MeOEt | H | Ph |
| 1-21 | m-NO₂Ph | 2-EtOEt | H | Ph |
| 1-22 | m-NO₂Ph | 2-PrOEt | H | Ph |
| 1-23 | m-NO₂Ph | 2-MeSEt | H | Ph |
| 1-24 | m-NO₂Ph | 2-EtSEt | H | Ph |
| 1-25 | m-NO₂Ph | 3-MeSPr | H | Ph |
| 1-26 | m-NO₂Ph | cPn | H | Ph |
| 1-27 | m-NO₂Ph | cHx | H | Ph |
| 1-28 | m-NO₂Ph | cPrMe- | H | Ph |
| 1-29 | m-NO₂Ph | cPnMe- | H | Ph |
| 1-30 | m-NO₂Ph | cHxMe- | H | Ph |
| 1-31 | m-NO₂Ph | All | H | Ph |
| 1-32 | m-NO₂Ph | Bun | H | Ph |
| 1-33 | m-NO₂Ph | Cim | H | Ph |
| 1-34 | o-TFMPh | Me | H | Ph |
| 1-35 | o-TFMPh | iPr | H | Ph |
| 1-36 | o-TFMPh | Hx | H | Ph |
| 1-37 | o-TFMPh | 2-MeOEt | H | Ph |
| 1-38 | m-TFMPh | Me | H | Ph |
| 1-39 | m-TFMPh | iPr | H | Ph |
| 1-40 | m-TFMPh | Hx | H | Ph |
| 1-41 | m-TFMPh | Cim | H | Ph |
| 1-42 | o-DFMOPh | Me | H | Ph |
| 1-43 | o-DFMOPh | Et | H | Ph |
| 1-44 | o-DFMOPh | iPr | H | Ph |
| 1-45 | o-CNPh | Me | H | Ph |
| 1-46 | o-CNPh | iPr | H | Ph |
| 1-47 | o-CNPh | Hx | H | Ph |
| 1-48 | m-CNPh | Me | H | Ph |
| 1-49 | m-CNPh | iPr | H | Ph |
| 1-50 | m-CNPh | Hx | H | Ph |
| 1-51 | m-CNPh | 2-MeOEt | H | Ph |
| 1-52 | o-ClPh | Me | H | Ph |
| 1-53 | o-ClPh | Et | H | Ph |
| 1-54 | o-ClPh | iPr | H | Ph |
| 1-55 | o-ClPh | Hx | H | Ph |
| 1-56 | o-ClPh | Cim | H | Ph |
| 1-57 | 2,3-diClPh | Me | H | Ph |
| 1-58 | 2,3-diClPh | Et | H | Ph |
| 1-59 | 2,3-diClPh | iPr | H | Ph |
| 1-60 | 2,3-diClPh | Hx | H | Ph |
| 1-61 | 2,3-diClPh | 2-MeOEt | H | Ph |
| 1-62 | 2,3-diClPh | cHx | H | Ph |
| 1-63 | 2,3-diClPh | All | H | Ph |
| 1-64 | 2,3-diClPh | Bun | H | Ph |
| 1-65 | 2,3-diClPh | Cim | H | Ph |
| 1-66 | m-NO₂Ph | Me | H | p-FPh |
| 1-67 | m-NO₂Ph | Et | H | p-FPh |
| 1-68 | m-NO₂Ph | iPr | H | p-FPh |
| 1-69 | m-NO₂Ph | Hx | H | p-FPh |
| 1-70 | m-NO₂Ph | Me | H | p-ClPh |
| 1-71 | m-NO₂Ph | iPr | H | p-ClPh |
| 1-72 | m-NO₂Ph | cHx | H | p-ClPh |
| 1-73 | m-NO₂Ph | Et | H | p-TFMPh |
| 1-74 | m-NO₂Ph | iPr | H | p-TFMPh |
| 1-75 | m-NO₂Ph | 2-MeOEt | H | p-TFMPh |
| 1-76 | 2,3-diClPh | iPr | H | p-FPh |
| 1-77 | m-NO₂Ph | Me | H | p-MePh |
| 1-78 | m-NO₂Ph | iPr | H | p-MeOPh |
| 1-79 | m-NO₂Ph | Hx | H | p-MeOPh |
| 1-80 | m-NO₂Ph | Me | 3-Me | Ph |
| 1-81 | m-NO₂Ph | Et | 3-Me | Ph |
| 1-82 | m-NO₂Ph | iPr | 3-Me | Ph |
| 1-83 | m-NO₂Ph | Hx | 3-Me | Ph |
| 1-84 | m-NO₂Ph | Cim | 3-Me | Ph |
| 1-85 | m-NO₂Ph | iPr | 3-Me | p-FPh |
| 1-86 | 2,3-diClPh | iPr | 3-Me | Ph |
| 1-87 | 2,3-diClPh | Hx | 3-Me | Ph |
| 1-88 | m-NO₂Ph | iPr | 2-Me | Ph |
| 1-89 | m-NO₂Ph | Hx | 2-Me | Ph |
| 1-90 | 2,3-diClPh | Me | 2-Me | p-FPh |
| 1-91 | 2,3-diClPh | iPr | 2-Me | Ph |

TABLE 2

| Compound No. | Ar | R | R¹ | R² |
|---|---|---|---|---|
| 2-1 | o-NO₂Ph | Me | H | Ph |
| 2-2 | o-NO₂Ph | Et | H | Ph |
| 2-3 | o-NO₂Ph | iPr | H | Ph |
| 2-4 | o-NO₂Ph | Hx | H | Ph |
| 2-5 | o-NO₂Ph | cHx | H | Ph |
| 2-6 | m-NO₂Ph | Me | H | Ph |
| 2-7 | m-NO₂Ph | Et | H | Ph |
| 2-8 | m-NO₂Ph | iPr | H | Ph |
| 2-9 | m-NO₂Ph | Hx | H | Ph |
| 2-10 | m-NO₂Ph | 6-HOHx | H | Ph |
| 2-11 | m-NO₂Ph | 2-MeOEt | H | Ph |
| 2-12 | m-NO₂Ph | 2-MeSEt | H | Ph |
| 2-13 | m-NO₂Ph | cPn | H | Ph |
| 2-14 | m-NO₂Ph | cPrMe- | H | Ph |
| 2-15 | m-NO₂Ph | Bun | H | Ph |
| 2-16 | m-NO₂Ph | Cim | H | Ph |
| 2-17 | 2,3-diClPh | Me | H | Ph |
| 2-18 | 2,3-diClPh | Et | H | Ph |
| 2-19 | 2,3-diClPh | iPr | H | Ph |
| 2-20 | 2,3-diClPh | Hx | H | Ph |
| 2-21 | 2,3-diClPh | 2-MeOEt | H | Ph |
| 2-22 | 2,3-diClPh | All | H | Ph |
| 2-23 | 2,3-diClPh | Cim | H | Ph |
| 2-24 | m-TFMPh | Me | H | Ph |
| 2-25 | m-TFMPh | iPr | H | Ph |
| 2-26 | m-NO₂Ph | Me | H | p-FPh |
| 2-27 | m-NO₂Ph | Et | H | p-FPh |
| 2-28 | m-NO₂Ph | iPr | H | p-FPh |
| 2-29 | m-NO₂Ph | Hx | H | p-FPh |
| 2-30 | m-NO₂Ph | 2-MeOEt | H | p-FPh |
| 2-31 | m-NO₂Ph | Me | H | p-ClPh |
| 2-32 | m-NO₂Ph | 6-HOHx | H | p-ClPh |
| 2-33 | m-NO₂Ph | Et | H | p-MePh |
| 2-34 | m-NO₂Ph | Bun | H | p-MePh |
| 2-35 | m-NO₂Ph | iPr | H | p-TFMPh |
| 2-36 | m-NO₂Ph | Cim | H | p-TFMPh |

TABLE 2-continued

| Compound No. | Ar | R | R¹ | R² |
|---|---|---|---|---|
| 2-37 | 2,3-diClPh | Me | H | p-FPh |
| 2-38 | 2,3-diClPh | iPr | H | p-FPh |
| 2-39 | 2,3-diClPh | Hx | H | p-FPh |
| 2-40 | m-NO₂Ph | Me | 3-Me | Ph |
| 2-41 | m-NO₂Ph | iPr | 3-Me | Ph |
| 2-42 | m-NO₂Ph | Hx | 3-Me | Ph |
| 2-43 | m-NO₂Ph | iPr | 3-Me | p-FPh |
| 2-44 | 2,3-diClPh | Me | 3-Me | Ph |
| 2-45 | 2,3-diClPh | iPr | 3-Me | Ph |
| 2-46 | m-NO₂Ph | iPr | 4-Me | Ph |
| 2-47 | m-NO₂Ph | Hx | 4-Me | Ph |
| 2-48 | 2,3-diClPh | Me | 4-Me | Ph |
| 2-49 | 2,3-diClPh | iPr | 4-Me | Ph |

TABLE 3

| Compound No. | Ar | R | R¹ | R² |
|---|---|---|---|---|
| 3-1 | o-NO₂Ph | Me | H | Ph |
| 3-2 | o-NO₂Ph | Et | H | Ph |
| 3-3 | o-NO₂Ph | iPr | H | Ph |
| 3-4 | o-NO₂Ph | Hx | H | Ph |
| 3-5 | o-NO₂Ph | cPn | H | Ph |
| 3-6 | m-NO₂Ph | Me | H | Ph |
| 3-7 | m-NO₂Ph | Et | H | Ph |
| 3-8 | m-NO₂Ph | iPr | H | Ph |
| 3-9 | m-NO₂Ph | Hx | H | Ph |
| 3-10 | m-NO₂Ph | 6-HOHx | H | Ph |
| 3-11 | m-NO₂Ph | 2-MeOEt | H | Ph |
| 3-12 | m-NO₂Ph | 2-MeSEt | H | Ph |
| 3-13 | m-NO₂Ph | cHx | H | Ph |
| 3-14 | m-NO₂Ph | cPrMe- | H | Ph |
| 3-15 | m-NO₂Ph | All | H | Ph |
| 3-16 | m-NO₂Ph | Cim | H | Ph |
| 3-17 | 2,3-diClPh | Me | H | Ph |
| 3-18 | 2,3-diClPh | Et | H | Ph |
| 3-19 | 2,3-diClPh | iPr | H | Ph |
| 3-20 | 2,3-diClPh | Hx | H | Ph |
| 3-21 | 2,3-diClPh | 2-MeOEt | H | Ph |
| 3-22 | 2,3-diClPh | Bun | H | Ph |
| 3-23 | 2,3-diClPh | Cim | H | Ph |
| 3-24 | m-TFMPh | Me | H | Ph |
| 3-25 | m-TFMPh | iPr | H | Ph |
| 3-26 | m-CHF₂OPh | iPr | H | Ph |
| 3-27 | m-CHF₂OPh | Hx | H | Ph |
| 3-28 | m-NO₂Ph | Me | H | p-FPh |
| 3-29 | m-NO₂Ph | Et | H | p-FPh |
| 3-30 | m-NO₂Ph | iPr | H | p-FPh |
| 3-31 | m-NO₂Ph | Hx | H | p-FPh |
| 3-32 | m-NO₂Ph | Me | H | p-ClPh |
| 3-33 | m-NO₂Ph | iPr | H | p-ClPh |
| 3-34 | m-NO₂Ph | iPr | H | p-MePh |
| 3-35 | m-NO₂Ph | Hx | H | p-MePh |
| 3-36 | m-NO₂Ph | Et | H | p-TFMPh |
| 3-37 | m-NO₂Ph | iPr | H | p-TFMPh |
| 3-38 | 2,3-diClPh | Me | H | p-FPh |
| 3-39 | 2,3-diClPh | iPr | H | p-FPh |
| 3-40 | 2,3-diClPh | Hx | H | p-FPh |
| 3-41 | m-NO₂Ph | Me | 3-Me | Ph |
| 3-42 | m-NO₂Ph | Et | 3-Me | Ph |
| 3-43 | m-NO₂Ph | iPr | 3-Me | Ph |
| 3-44 | m-NO₂Ph | Hx | 3-Me | Ph |
| 3-45 | m-NO₂Ph | Me | 3-Me | p-FPh |
| 3-46 | 2,3-diClPh | Me | 3-Me | Ph |
| 3-47 | 2,3-diClPh | iPr | 3-Me | Ph |
| 3-48 | m-NO₂Ph | iPr | 4-Me | Ph |
| 3-49 | m-NO₂Ph | Hx | 4-Me | Ph |

TABLE 4

| Compound No. | Ar | R | R¹ | R² |
|---|---|---|---|---|
| 4-1 | m-NO₂Ph | Me | H | Ph |
| 4-2 | m-NO₂Ph | Et | H | Ph |
| 4-3 | m-NO₂Ph | iPr | H | Ph |
| 4-4 | m-NO₂Ph | Hx | H | Ph |
| 4-5 | m-NO₂Ph | 2-MeOEt | H | Ph |
| 4-6 | m-NO₂Ph | Bun | H | Ph |
| 4-7 | m-NO₂Ph | Cim | H | Ph |
| 4-8 | m-NO₂Ph | Me | H | p-FPh |
| 4-9 | m-NO₂Ph | iPr | H | p-FPh |
| 4-10 | 2,3-diClPh | Me | H | Ph |
| 4-11 | 2,3-diClPh | Et | H | Ph |
| 4-12 | 2,3-diClPh | iPr | H | Ph |
| 4-13 | 2,3-diClPh | Hx | H | Ph |
| 4-14 | o-NO₂Ph | Me | H | Ph |
| 4-15 | o-NO₂Ph | iPr | H | Ph |
| 4-16 | m-NO₂Ph | Me | 3-Me | Ph |
| 4-17 | m-NO₂Ph | iPr | 3-Me | Ph |

TABLE 5

| Compound No. | Ar | R | R¹ | R² |
|---|---|---|---|---|
| 5-1 | m-NO₂Ph | Me | H | Ph |
| 5-2 | m-NO₂Ph | Et | H | Ph |
| 5-3 | m-NO₂Ph | iPr | H | Ph |
| 5-4 | m-NO₂Ph | Hx | H | Ph |
| 5-5 | m-NO₂Ph | All | H | Ph |
| 5-6 | m-NO₂Ph | Et | H | p-FPh |
| 5-7 | m-NO₂Ph | iPr | H | p-FPh |
| 5-8 | 2,3-diClPh | Me | H | Ph |
| 5-9 | 2,3-diClPh | iPr | H | Ph |
| 5-10 | 2,3-diClPh | Hx | H | Ph |
| 5-11 | 2,3-diClPh | 5-HOPn | H | Ph |
| 5-12 | o-NO₂Ph | Et | H | Ph |
| 5-13 | o-NO₂Ph | iPr | H | Ph |
| 5-14 | m-NO₂Ph | Me | 3-Me | Ph |
| 5-15 | m-NO₂Ph | iPr | 4-Me | Ph |

TABLE 6

| Compound No. | Ar | R | R¹ | R² |
|---|---|---|---|---|
| 6-1 | m-NO₂Ph | Me | H | Ph |
| 6-2 | m-NO₂Ph | Et | H | Ph |
| 6-3 | m-NO₂Ph | iPr | H | Ph |
| 6-4 | m-NO₂Ph | Hx | H | Ph |
| 6-5 | m-NO₂Ph | 6-HOHx | H | Ph |
| 6-6 | m-NO₂Ph | Cim | H | Ph |
| 6-7 | m-NO₂Ph | Me | H | p-FPh |
| 6-8 | m-NO₂Ph | iPr | H | p-FPh |
| 6-9 | 2,3-diClPh | Et | H | Ph |
| 6-10 | 2,3-diClPh | iPr | H | Ph |
| 6-11 | 2,3-diClPh | Hx | H | Ph |
| 6-12 | o-NO₂Ph | Me | H | Ph |
| 6-13 | o-NO₂Ph | iPr | H | Ph |
| 6-14 | m-NO₂Ph | Me | 3-Me | Ph |
| 6-15 | m-NO₂Ph | iPr | 3-Me | Ph |

TABLE 7

| Compound No. | n | R²ᵇ |
|---|---|---|
| 7-1 | 1 | 4-FPh |
| 7-2 | 1 | 4-ClPh |
| 7-3 | 2 | 4-FPh |
| 7-4 | 2 | 4-ClPh |
| 7-5 | 3 | 4-FPh |
| 7-6 | 3 | 4-ClPh |

Of the compounds listed above, the following are preferred, that is to say Compounds No.

1-9. 3-(1-Benzhydryl-3-azetidinyl) 5-ethyl 2-amino-6-methyl-4-(3-nitrophenyl)-1,4-dihydropyridine-3,5-dicarboxylate and salts thereof;

1-11. 3-(1-Benzhydryl-3-azetidinyl) 5-isopropyl 2-amino-6-methyl-4-(3-nitrophenyl)-1,4-dihydropyridine-3,5-dicarboxylate and salts thereof, especially its dihydrochloride;

1-27. 3-(1-Benzhydryl-3-azetidinyl) 5-cyclohexyl 2-amino-6-methyl-4-(3-nitrophenyl)-1,4-dihydropyridine-3,5-dicarboxylate and salts thereof, especially its dihydrochloride;

1-59. 3-(1-Benzhydryl-3-azetidinyl) 5-isopropyl 2-amino-4-(2,3-dichlorophenyl)-6-methyl-1,4-dihydropyridine-3,5-dicarboxylate and salts thereof;

1-68. 3-[1-(4,4'-Difluorobenzhydryl)-3-azetidinyl]5-isopropyl 2-amino-6-methyl-4-(3-nitrophenyl)-1,4-dihydropyridine-3,5-dicarboxylate and salts thereof;

1-82. 3-(1-Benzhydryl-3-methyl-3-azetidinyl) 5-isopropyl 2-amino-6-methyl-4-(3-nitrophenyl)-1,4-dihydropyridine-3,5-dicarboxylate and salts thereof;

2-8. 3-(1-Benzhydryl-3-pyrrolidinyl) 5-isopropyl 2-amino-6-methyl-4-(3-nitrophenyl)-1,4-dihydropyridine-3,5-dicarboxylate and salts thereof, especially its dihydrochloride;

2-9. 3-(1-Benzhydryl-3-pyrrolidinyl) 5-hexyl 2-amino-6-methyl-4-(3-nitrophenyl)-1,4-dihydropyridine-3,5-dicarboxylate and salts thereof, especially its dihydrochloride;

3-8. 3-(1-Benzhydryl-3-piperidyl) 5-isopropyl 2-amino-6-methyl-4-(3-nitrophenyl)-1,4-dihydropyridine-3,5-dicarboxylate and salts thereof, especially its dihydrochloride; and 4-3. 3-Isopropyl 5-(1-benzhydryl-3-azetidinyl) 2-amino-6-methyl-4-(3-nitrophenyl)-1,4-dihydropyridine-3,5-dicarboxylate.

Of these, Compounds No. 1-11, 1-59 and 1-68 are most preferred.

The compounds of formula (I) in accordance with the present invention can be prepared, for example, by the following reaction, specifically, they can be prepared by reacting an α-benzylideneacetoacetic acid ester of formula (II):

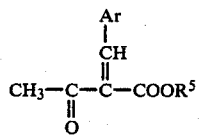

with an amidinoacetic acid ester of formula (III):

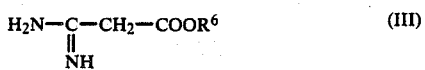

In the above formulae, Ar is as defined above and one of $R^5$ and $R^6$ represents a group of formula (IV):

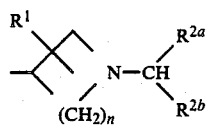

(in which n, $R^1$, $R^{2a}$ and $R^{2b}$ are as defined above) and the other of $R^5$ and $R^6$ represents a $C_1$-$C_{16}$ alkyl group, a $C_3$-$C_6$ cycloalkyl group, a $C_1$-$C_4$ alkyl group having a $C_3$-$C_6$ cycloalkyl substituent, a $C_2$-$C_4$ alkenyl group, a cinnamyl group or a $C_1$-$C_{16}$ alkyl group having at least one substituent selected from the group consisting of hydroxy, $C_1$-$C_4$ alkoxy and $C_1$-$C_4$ alkylthio groups, i.e. any one of the groups defined above in respect of R.

More specifically, the reaction involved in the preparation of the compounds of the invention may be as illustrated below in order to prepare the compounds of formulae (Ia) and (Ib), respectively:

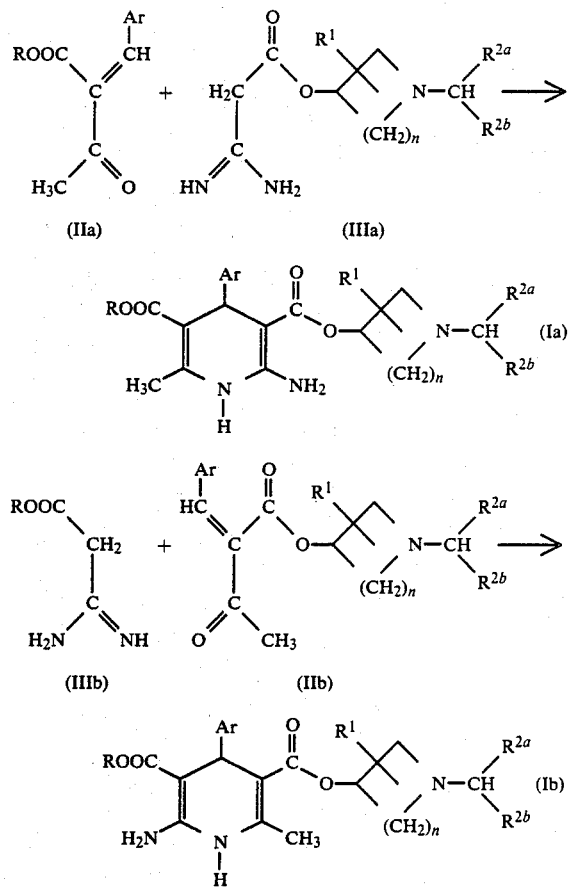

In the above formulae, Ar, n, R, $R^1$, $R^{2a}$ and $R^{2b}$ are as defined above.

In order to carry out this reaction, the compound of formula (II), (IIa) or (IIb) is mixed with the compound of formula (III), (IIIa) or (IIIb), preferably in equimolar amounts, although a greater than equimolar amount of either of the reagents may be employed, if desired. However, this tends to be wasteful of reagents and so equimolar proportions are preferred. The reaction is preferably carried out in the presence of a solvent, more preferably an organic solvent, for example: an alcohol, such as ethanol, isopropanol or t-butanol; an ether, such as dioxane; a fatty acid amide, such as dimethylformamide; a sulfoxide, such as dimethyl sulfoxide; or a nitrile, such as acetonitrile; or in the presence of water; or a mixture of any two or more thereof. Alternatively, the reaction may be effected in the absence of a solvent.

The reaction will take place over a wide range of temperatures, and the precise temperature chosen is not critical to the present invention. However, we generally find it convenient to carry out the reaction at about room temperature or with heating, preferably at or about the reflux temperature of the reaction mixture, and normally at or about the reflux temperature of the solvent employed. Normally, we prefer to carry out the reaction under atmospheric pressure or under superatmospheric pressure. Most conveniently, the reaction is carried out in the presence of one or more of the above solvents under atmospheric pressure and at around the boiling point of the solvent employed.

The reaction time will vary depending upon many factors, notably the reaction temperature, and is not critical to the practice of the present invention. However, at the temperatures suggested above, a period of from 30 minutes to five hours will usually suffice.

In this reaction, the compound of formula (III), (IIIa) or (IIIb) is preferably used in the form of an acid addition salt, such as the hydrochloride, hydrobromide or acetate and, in that case, the reaction is preferably carried out in the presence of a base, preferably an equimolar amount of a base, and preferably an alkali metal (e.g. sodium or potassium) alkoxide, such as sodium methoxide or sodium ethoxide.

After completion of the reaction, the desired compound of formula (I), (Ia) or (Ib) may be recovered from the reaction mixture by conventional means, and, if necessary, it may be further purified by such conventional purification techniques as recrystallization or the various chromatography techniques, notably column chromatography.

Of the starting materials employed in the reactions described above, the compound of formula (IIa) may be prepared by the dehydrating condensation of an aldehyde of formula Ar—CHO with an acetoacetic acid ester of formula $CH_3COCH_2COOR$ according to a known method [e.g., G. Jones, "Knoevenagel Condensation", Org. Reactions, Volume 15, 204 (1967)]. The acetoacetic ester employed in this reaction may be prepared from diketene and an alcohol of formula R—OH according to a known method [e.g., A. B. Boese, Jr., Industrial and Engineering Chemistry, 32, 16 (1940)].

The compound of formula (IIIa) can easily be prepared by reacting a cyanoacetic acid ester of formula (V):

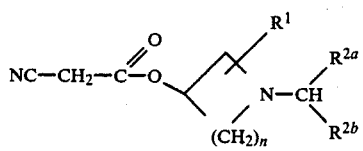

(in which n, $R^1$, $R^{2a}$ and $R^{2b}$ are as defined above) with ammonia or with an ammonium salt according to a known method [S. A. Glickman and A. C. Cope, J. Amer. Chem. Soc., 67, 1017 (1945); S. M. McElvain and B. E. Tate, J. Amer. Chem. Soc., 73, 2760 (1951)].

The compound of formula (V) can be prepared by a conventional esterification between cyanoacetic acid and an alcohol of formula (VI):

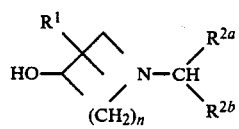

(in which n, $R^1$, $R^{2a}$ and $R^{2b}$ are as defined above), e.g. a dehydration reaction catalyzed with an acid or in the presence of a carbodiimide, such as 1,3-dicyclohexyl-carbodiimide.

The alcohol of formula (VI) can easily be prepared by reacting a cyclic amine of formula (VII):

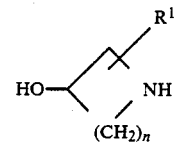

(in which n and $R^1$ are as defined above) with an optionally substituted benzhydryl halide of formula (VIII):

(in which $R^{2a}$ and $R^{2b}$ are as defined above and X represents a halogen atom).

The alcohol of formula (VI) in which n is 1 can be prepared from epichlorohydrin and benzhydrylamine according to a known method [A. G. Anderson, Jr. and R. Lok., J. Org. Chem., 37, 3953 (1972)].

Compounds of formula (VI) in which $R^1$ represents a $C_1$-$C_3$ alkyl group on the 3-position of the nitrogen-containing heterocyclic ring (i.e. on the same carbon atom as the hydroxy group), that is to say compounds of formula (VIc), may also be prepared as illustrated by the following reaction scheme:

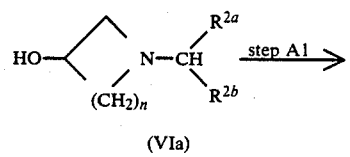

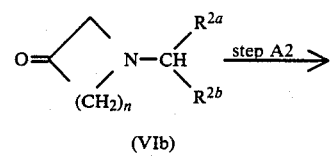

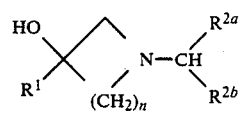

(in which n, $R^1$, $R^{2a}$ and $R^{2b}$ are as defined above).

Step A1 of the above reaction scheme, in which the hydroxy group is oxidized to a ketonic oxo group, may be carried out as described by A. Morimoto et al. [Chem. Pharm. Bull., 21, (1), 228–231 (1973)] and D. Horton et al. [Carbohydr. Res., 7, 56 (1968)]. Step A2 of the reaction scheme involves the reaction of the compound of formula (VIb), prepared in Step A1, with a Grignard compound of formula $R^1MgX'$ (in which $R^1$ is as defined above and X' represents halogen atom, preferably a chlorine, iodine or bromine atom), as described by S. S. Chatterjee et al. [Synthesis, 1973, 153–154]

Compounds of formulae (IIb) and (IIIb) may be prepared by methods analogous to those used to prepare the compounds of formulae (IIa) and (IIIa), respectively, e.g. as illustrated by the following reaction schemes:

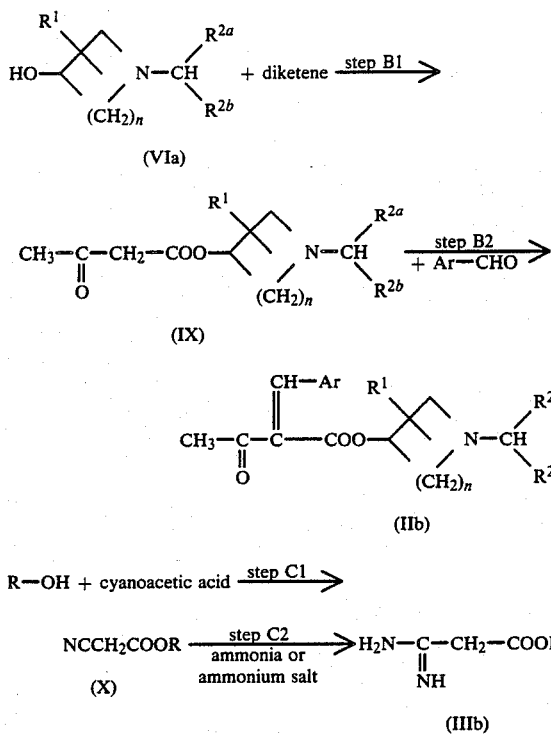

In the above formulae, Ar, n, R, $R^1$, $R^{2a}$ and $R^{2b}$ are as defined above.

Steps B1 and B2 of this reaction scheme consist of the reaction of a compound of formula (VIa) with diketene and then the reaction of the resulting acetoacetate compound of formula (IX) with a compound of formula Ar—CHO, in a similar manner to that described for the synthesis of the compound of formula (IIa). Steps C1 and C2 of the reaction scheme consist of the reaction of an alcohol of formula R—OH with cyanoacetic acid and then reaction of the resulting cyanoacetate (X) with ammonia or with an ammonium salt in a similar manner to that described for the synthesis of the compound of formula (IIIa).

Compounds of formulae (Ia) and (Ib) synthesized according to the reactions described above can form a number of stereoisomers, for example optical isomers, because of the presence in their molecules of a number of asymmetric carbon atoms, e.g. at the 4-position of the dihydropyridine ring or in the alcohol moiety which forms the ester group. Geometric isomers (cis or trans) may also be formed in some cases as a result of the same alcohol moiety. The individual isolated isomers may, in some cases, be prepared by stereospecific synthesis techniques or they may be isolated by methods known per se from mixtures of isomers. The present invention embraces both the individual isolated isomers and mixtures of isomers.

BIOLOGICAL ACTIVITY

The dihydropyridine derivatives of the present invention exhibit significant calcium antagonism and antihypertensive activity as shown below.

1. Calcium Antagonism

An isolated rat aorta was suspended in a calcium-free and high potassium Krebs-Henseleit solution maintained at a temperature of 37° C. The contractile response of the aorta to calcium chloride in concentrations ranging from $10^{-5}$ to $10^{-2}$M was recorded by means of an isometric transducer. The dose-response curve of the aorta was obtained before and after addition of a test compound at a concentration of 5 nM. Addition of the test compound shifted the dose-response curve to the right, the magnitude of the shift depending upon the potency of the $Ca^{++}$-blocking activity. The test compounds showed a significant rightwards movement and, for example, that of Compound No. 1-11 (see foregoing Table 1), i.e. the compound of Example 1, was comparable with that of nifedipine, and had excellent duration of activity.

2. Antihypertensive activity

The test animals were spontaneously hypertensive rats of the SHR strain, each aged about 15 weeks. The antihypertensive activities of the test compounds were determined in these rats as follows.

Each animal was anaesthetized with sodium pentobarbital (50 mg/kg, intraperitoneally) and a polyethylene cannula was inserted into the abdominal aorta by the method of Weeks and Jones [J. R. Weeks and J. A. Jones, Proc. Soc. Exptl. Biol. Med., 104, 646–648 (1960)]. The other end of the cannula left the animal's body at, and was fixed to, the neck. About 1 week after this surgery, when the animal had completely recovered from surgical stress, the free end of the aortic cannula was connected to a sphygmomanmeter to measure blood pressure and heart rate of the animal directly in the conscious, aparalytic and unrestrained state.

The blood pressure and heart rate were monitored, and, when these had stabilized, which was after about 1 hour, the stable values were recorded as control values. At this time, a test compound suspended in a 0.3% w/v aqueous carboxymethylcellulose solution was administered orally in the dose shown in the following Table 8. The blood pressure and heart rate were then recorded every 15 minutes during the 24 hours after administration of the test compound.

The experiment was carried out with Compounds No. 1-11, 1-59, 1-68, 2-8 and 3-8 (see foregoing Tables 1, 2 and 3) as well as with nifedipine and nicardipine, and the results are recorded in the following Table 8.

TABLE 8

| Cpd. No. | Ex. No. | Dose (mg/kg, po) | 12 Hour Area | $T_{max}$ (hours) | $T_{0.5\ max}$ (hours) |
|---|---|---|---|---|---|
| 1-11 | 1 | 1 | −184 | 6.0 | 10.4 |
| 1-11 | 1 | 3 | −334 | 5.0 | 12.7 |
| 1-59 | 7 | 1 | −203 | 6.0 | 12.0 |
| 1-68 | 11 | 1 | −218 | 7.0 | 11.8 |
| 2-8 | 14 | 1 | −172 | 6.0 | 11.2 |
| 3-8 | 16 | 1 | −141 | 7.0 | 11.4 |
| nifedipine | — | 3 | −237 | 0.3 | 7.0 |
| nicardipine | — | 3 | −175 | 0.5 | 5.3 |

In the above Table, the results are reported as follows:

$T_{max}$: the time in hours after administration of the compound under test before the maximum change in blood pressure was recorded;

$T_{0.5\ max}$: the time in hours after administration of the compound under test which is required for the blood pressure to return to one half of its maximum value;

12 hour area: the integrated value of the area above the graph of blood pressure change against time after administration of the compound under test over a period of 12 hours after administration to show the potency of the blood pressure lowering action.

Although the maximum levels of hypotension produced by all of the compounds of the invention tested were found to be comparable with those produced by nifedipine and nicardipine, there was a considerable difference in the time of onset of activity and in the duration of activity between the compounds of the present invention and the prior art compounds used for comparison. As is obvious from the results reported in Table 8, Compound 1-11 lowered blood pressure much more slowly than did nifedipine or nicardipine. Also the duration of the antihypertensive activity produced by Compound 1-11 was much longer than that produced by nifedipine and nicardipine. In addition, nifedipine (but not Compound 1-11) increased heart rate, which was most probably caused by a baroreceptor reflex due to the abrupt reduction in blood pressure. Similarly good results were achieved with the other compounds of the invention which we tested.

Accordingly, the compounds of the invention and pharmaceutically acceptable acid addition salts thereof can be used for the treatment of cardiovascular diseases, such as hypertension, angina pectoris miocardial infarction, arrhythmia, arteriosclerosis and cerebrovascular disorders, such as cerebral ischemia.

The compounds may be administered in any suitable form, depending upon the nature and condition of the patient, the nature of the disorder and the desired route of administration. For example, the compounds may be administered orally in the form of tablets, capsules, granules, powders or syrups. Alternatively, the compounds may be administered non-orally by, for example, subcutaneous injection, intravenous injection or suppository. The compounds may, if desired, be mixed with carriers, excipients or other auxiliary substances commonly employed in the formulation of pharmaceutical preparations, for example diluents, binders, disintegrating agents, lubricants, flavors, solubilizers and suspending agents. The dose will vary, depending upon the symptoms, age and body weight of the patient, as well as the nature and severity of the disease or disorder to be treated; however, a dose of from 3 to 300 mg per day will normally be appropriate for an adult human patient, and this may be administered in a single dose or in divided doses.

The invention is further illustrated with reference to the following Examples. Preparation of certain of the starting materials employed in these Examples is also illustrated in the subsequent Preparations.

EXAMPLE 1

3-(1-Benzhydryl-3-azetidinyl) 5-isopropyl 2-amino-6-methyl-4-(3-nitrophenyl)-1,4-dihydropyridine-3,5-dicarboxylate and its dihydrochloride Preparation of free base 0.27 g (0.005 mole) of sodium methoxide was added to a solution of 1.39 g (0.005 mole) of isopropyl 2-(3-nitrobenzylidene)acetoacetate and 1.62 g (0.005 mole) of the acetic acid salt of 1-benzhydryl-3-azetidinyl amidinoacetate (prepared as described in Preparation 2) dissolved in 80 ml of isopropanol, and the mixture was heated under reflux for 4 hours. At the end of this time, the mixture was cooled, insoluble materials were filtered off and the filtrate was concentrated by evaporation under reduced pressure. The residue was dissolved in ethyl acetate and washed with water, after which it was dried over anhydrous sodium sulfate. The solvent was then removed by distillation under reduced pressure, and the residue was subjected to column chromatography through silica gel, using a 3:1 by volume mixture of toluene and ethyl acetate as eluent, to give 2.17 g (yield 74%) of the title compound (a free base) as pale yellow crystals, melting at 95°–98° C.

Infrared Absorption Spectrum (KBr) $\nu_{max}$ cm$^{-1}$: 3450, 3310 (NH), and 1675 (—CO$_2$—).

Mass Spectrum (CI) m/e: 583 (M$^+$+1), 344 (M$^+$—benzhydrylazetidinyloxy) and 167 [+CH(phenyl)$_2$].

Nuclear Magnetic Resonance Spectrum: (CDCl$_3$) δ ppm: 1.08, 1.26 (6H, 2×doublet, J=6 Hz); 2.35 (3H, singlet); 2.63, 3.06, 3.50, 3.62 (4H, 4×triplet, J=8 Hz); 4.26 (1H, singlet); 4.87–5.04 (3H, multiplet); 6.04 (1H, broad singlet); 6.11 (2H, broad singlet); 7.1–8.17 (14H, multiplet).

The resulting free base was recrystallized from a mixture of benzene and hexane to afford pale yellow crystals, melting at 120°–124° C.

The free base was also recrystallized from a mixture of 1,2-dimethoxyethane and hexane to afford pale yellow crystals melting at 162.5°–164.5° C. The crystals contained an equimolar amount of 1,2-dimethoxyethane (determined by NMR spectrum). These crystals were dried above 100° C. under reduced pressure, giving the desired compound as yellow crystals melting at 158°–160° C.

Both kinds of crystals described above melting at 120°–124° C. and at 158°–160° C. were identified with the free base by NMR spectroscopy.

Elemental analysis: Calculated for C$_{33}$H$_{34}$N$_4$O$_6$: C, 68.03%, H, 5.88%; N, 9.62%. Found: C, 68.36%; H, 5.94%; N, 9.20%. (free base) C, 68.49%; H, 5.71%; N, 9.62%. (after recrystallization from a mixture of benzene and hexane) C, 67.94%, H, 5.91%, N, 9.63 (after recrystallization from a mixture of 1,2-dimethoxyethane and hexane and drying at about 100° C. under reduced pressure).

Preparation of dihydrochloride

Hydrogen chloride was bubbled into a solution of 0.87 g of the free base in 20 ml of chloroform for 5 minutes. At the end of this time, the solvent was removed by evaporation under reduced pressure, giving 0.95 g of the title compound dihydrochloride as pale yellow crystals, melting at 118°–120° C.

Infrared Absorption Spectrum: (KBr) $\nu_{max}$ cm$^{-1}$: 3400, 3280 (NH) and 1685 (—CO$_2$—).

Mass Spectrum: m/e: 583 (M$^+$+1), 539 [M$^+$—CH(CH$_3$)$_2$], and 167 [+CH(phenyl)$_2$].

Elemental analysis: Calculated for C$_{33}$H$_{36}$N$_4$O$_6$Cl$_2$: C, 60.46%; H, 5.53%; N, 8.55%. Found: C, 60.59%; H, 5.81%; N, 8.44%.

EXAMPLES 2–18

Following a procedure similar to that described in Example 1, the following compounds were obtained:

Example 2

3-(1-Benzhydryl-3-azetidinyl) 5-methyl 2-amino-6-methyl-4-(3-nitrophenyl)-1,4-dihyropyridine-3,5-dicarboxylate, melting at 88°–92° C.

Example 3

3-(1-Benzhydryl-3-azetidinyl) 5-hexyl 2-amino-6-methyl-4-(3-nitrophenyl)-1,4-dihyropyridine-3,5-dicarboxylate dihydrochloride, melting at 106°–108° C.

Example 4

3-(1-Benzhydryl-3-azetidinyl) 5-(2-methoxyethyl) 2-amino-6-methyl-4-(3-nitrophenyl)-1,4-dihydropyridine-3,5-dicarboxylate, melting at 83°–85° C.

Example 5

3-(1-Benzhydryl-3-azetidinyl) 5-cinnamyl 2-amino-6-methyl-4-(3-nitrophenyl)-1,4-dihydropyridine-3,5-dicarboxylate hydrate, melting at 114°–117° C.

Example 6

3-(1-Benzhydryl-3-azetidinyl) 5-cyclohexyl 2-amino-6-methyl-4-(3-nitrophenyl)-1,4-dihydropyridine-3,5-dicarboxylate dihydrochloride, melting at 113°–114.5° C.

Example 7

3-(1-Benzhydryl-3-azetidinyl) 5-isopropyl 2-amino-4-(2,3-dichlorophenyl)-6-methyl-1,4-dihydropyridine-3,5-dicarboxylate, melting at 100°–102° C.

Example 8

3-(1-Benzhydryl-3-azetidinyl) 5-isopropyl 2-amino-4-(2-chlorophenyl)-6-methyl-1,4-dihydropyridine-3,5-dicarboxylate, melting at 85°–88° C.

Example 9

3-(1-Benzhydryl-3-azetidinyl) 5-ethyl 2-amino-6-methyl-4-(3-nitrophenyl)-1,4-dihydropyridine-3,5-dicarboxylate hemihydrate, melting at 134°–136° C.

Example 10

3-(1-Benzhydryl-3-azetidinyl) 5-cyclopropylmethyl 2-amino-6-methyl-4-(3-nitrophenyl)-1,4-dihydropyridine-3,5-dicarboxylate, melting at 156°–160° C.

Example 11

3-[1-(4,4'-Difluorobenzhydryl)-3-azetidinyl] 5-isopropyl 2-amino-6-methyl-4-(3-nitrophenyl)-1,4-dihydropyridine-3,5-dicarboxylate, melting at 118°–120° C.

Example 12

3-(1-Benzhydryl-3-azetidinyl) 5-isopropyl 2-amino-6-methyl-4-(3-trifluoromethylphenyl)-1,4-dihydropyridine-3,5-dicarboxylate hydrate, melting at 96°–98° C.

Example 13

3-(1-Benzhydryl-3-azetidinyl) 5-isopropyl 2-amino-4-(3-cyanophenyl)-6-methyl-1,4-dihydropyridine-3,5-dicarboxylate hydrate, melting at 95°–97° C.

Example 14

3-(1-Benzhydryl-3-pyrrolidinyl) 5-isopropyl 2-amino-6-methyl-4-(3-nitrophenyl)-1,4-dihyropyridine-3,5-dicarboxylate dihydrochloride, melting at 166°–169° C.

Example 15

3-(1-Benzhydryl-3-pyrrolidinyl) 5-hexyl 2-amino-6-methyl-4-(3-nitrophenyl)-1,4-dihydropyridine-3,5-dicarboxylate dihydrochloride hydrate, melting at 104°–108° C.

Example 16

3-(1-Benzhydryl-3-piperidyl) 5-isopropyl 2-amino-6-methyl-4-(3-nitrophenyl)-1,4-dihydropyridine-3,5-dicarboxylate dihydrochloride hydrate, melting at 174°–177° C.

Example 17

3-(1-Benzhydryl-3-piperidyl) 5-hexyl 2-amino-6-methyl-4-(3-nitrophenyl)-1,4-dihydropyridine-3,5-dicarboxylate dihydrochloride hydrate, melting at 151°–155° C.

Example 18

3-(1-Benzhydryl-3-methyl-3-azetidinyl) 5-isopropyl 2-amino-6-methyl-4-(3-nitrophenyl)-1,4-dihydropyridine-3,5-dicarboxylate, melting at 116°–118° C.

EXAMPLE 19

3-Isopropyl 5-(1-benzhydryl-3-azetidinyl) 2-amino-6-methyl-4-(3-nitrophenyl)-1,4-dihydropyridine-3,5-dicarboxylate 1.6 g (0.0035 mole) of 1-benzhydryl-3-azetidinyl 2-(3-nitrobenzylidene)acetoacetate (prepared as described in Preparation 15) and 0.63 g (0.0035 mole) of isopropyl amidinoacetate hydrochloride were dissolved in 40 ml of isopropanol. 0.19 g (0.0035 mole) of sodium methoxide was then added to the mixture, and the mixture was heated under reflux for 4 hours. At the end of this time, the mixture was cooled, and the insoluble material was filtered off. The solvent was then distilled off under reduced pressure, and the residue was dissolved in ethyl acetate. The resulting solution was washed with water and dried over anhydrous sodium sulfate. The solvent was distilled off under reduced pressure. The residue was purified by silica gel column chromatography, using a 4:1 by volume mixture of toluene and ethyl acetate as eluent, to give 1.15 g (yield 56%) of the title compound as pale yellow crystals, melting at 104°–107° C.

Infrared Absorption Spectrum (KBr) $\nu_{max}$ cm$^{-1}$: 3440, 3320 (—NH), 1675 (—CO$_2$—).

Mass Spectrum (CI, m/e): 583 (M$^+$+1), 167 [+CH(phenyl)$_2$].

Nuclear Magnetic Resonance Spectrum (CDCl$_3$) δ ppm: 1.04, 1.30 (6H, 2×doublet, J=6 Hz); 2.32 (3H, singlet); 2.65, 3.00, 3.55 (4H, multiplet); 4.25 (1H, singlet); 4.85–5.05 (3H, multiplet); 6.05 (1H, broad singlet); 6.11 (2H, broad singlet); 7.1–8.15 (14H, multiplet).

Elemental analysis: Calculated for C$_{33}$H$_{34}$N$_4$O$_6$: C, 68.03%; H, 5.88%; N, 9.62%. Found: C, 68.12%; H, 5.99%; N, 9.40%.

EXAMPLES 20+21

The compounds described below were obtained in a similar manner to that described in Example 19.

Example 20

3-Isopropyl 5-(1-benzhydryl-3-pyrrolidinyl) 2-amino-6-methyl-4-(3-nitrophenyl)-1,4-dihydropyridine-3,5-dicarboxylate, melting at 107°–110° C.

Example 21

3-Isopropyl 5-(1-benzhydryl-3-piperidyl) 2-amino-6-methyl-4-(3-nitrophenyl)-1,4-dihydropyridine-3,5-dicarboxylate, melting at 112°–116° C.

PREPARATION 1

1-Benzhydryl-3-azetidinyl cyanoacetate 4.25 g (0.05 mole) of cyanoacetic acid and 11.95 g (0.05 mole) of 1-benzhydryl-3-hydroxyazetidine were dissolved in 400 ml of tetrahydrofuran. 12.38 g (0.06 mole) of 1,3-dicyclohexylcarbodiimide were then added to the solution, whilst stirring, after which the mixture was stirred at 55° C. for 11 hours. At the end of this time, the mixture was cooled, precipitated crystals were removed and the solvent was removed by distillation under reduced pressure. The residue was dissolved in ethyl acetate and the resulting solution was washed with water and then dried over anhydrous sodium sulfate.

The solution was then concentrated by evaporation under reduced pressure, and the residue was subjected to column chromatography through silica gel, using a 19:1 by volume mixture of toluene and ethyl acetate as eluent, to give 14.25 g (93%) of the title compound as a pale yellow oil.

Infrared Absorption Spectrum (capillary) $\nu_{max}$ cm$^{-1}$: 2250 (CN) and 1745 (—CO$_2$—).

Mass Spectrum m/e: 306 (M$^+$) and 167 [+CH(phenyl)$_2$].

Nuclear Magnetic Resonance Spectrum: (CDCl$_3$) δ ppm: 3.1 (2H, multiplet); 3.46 (2H, singlet); 3.6 (2H, multiplet); 4.37 (1H, singlet); 5.16 (1H, quartet, J=6 Hz); 7.1–7.5 (10H, multiplet).

PREPARATION 2

Acetic acid salt of 1-benzhydryl-3-azetidinyl amidinoacetate

A solution of 7.0 g (0.0229 mole) of 1-benzhydryl-3-azetidinyl cyanoacetate (prepared as described in Preparation 1) and 1.26 g (0.0275 mole) of ethanol dissolved in 300 ml of chloroform was cooled with a mixture of salt and ice. Hydrogen chloride was then bubbled into the solution for 30 minutes, whilst cooling, and the mixture was allowed to stand overnight, also whilst cooling. At the end of this time, the temperature of the mixture was allowed to rise to room temperature, and then the mixture was freed from the solvent by evaporation under reduced pressure. The residue was dissolved in 300 ml of chloroform and ammonia was bubbled into the solution for 1 hour, whilst ice cooling. The precipitated salt was removed by filtration, and the solvent was distilled off under reduced pressure. The residue was dissolved in 50 ml of acetonitrile, and 1.76 g (0.0229 mole) of ammonium acetate was then added to the solution. The mixture was stirred at 55° C. for 1 hour. At the end of this time, unreacted ammonium acetate was removed from the still hot reaction mixture by filtration, and the solvent was distilled off under reduced pressure. The residue was crystallized by adding diethyl ether, and the resulting crystals were collected by filtration and then dried under reduced pressure to afford 7.6 g (yield 87% based on the cyanoacetate) of the title compound as colorless crystals, melting at 100°–103° C.

Mass Spectrum m/e: 324 ($M^+ +1$) and 167 [$+CH(phenyl)_2$].

PREPARATION 3

1-(4,4'-Difluorobenzhydryl)-3-dydroxyazetidine 9.25 g (0.1 mole) of epichlorohydrin and 21.9 g (0.1 mole) of 4,4'-difluorobenzhydrylamine were dissolved in 100 ml of methanol. The mixture was stirred at room temperature whilst shading it from the light for 3 days. At the end of this time, the mixture was heated under reflux whilst stirring for 3 days. The methanol was then distilled off under reduced pressure, and the residue was dissolved in ethyl acetate. The solution was washed, first with 100 ml of a 10% w/v aqueous solution of sodium hydroxide and then twice, each time with 100 ml of water. The organic layer was dried over anhydrous sodium sulfate, and the solvent was distilled off under reduced pressure. The residue was purified by silica gel column chromatography, using a 3:2 by volume mixture of toluene and ethyl acetate as eluent, to give 6 g (yield 22%) of the title compound as a pale yellow oil.

Infrared Absorption Spectrum (capillary) $\nu_{max}$ cm$^{-1}$: 3360 (—OH).

Mass Spectrum (m/e): 275 ($M^+$), 203 [$+CH(p-fluorophenyl)_2$].

Nuclear Magnetic Resonance Spectrum (CDCl$_3$) δ ppm: 2.35 (1H, singlet); 2.86 (2H, multiplet); 3.46 (2H, multiplet); 4.30 (1H, singlet); 4.40 (1H, quintet, J=5 Hz); 6.88–7.35 (8H, multiplet).

PREPARATION 4

1-Benzhydryl-3-hydroxy-3-methylazetidine 7.17 g (0.03 mole) of 1-benzhydryl-3-hydroxyazetidine were dissolved in a mixture of 35 ml of dimethyl sulfoxide and 20 ml of methylene chloride. 1 ml of pyridine, 0.5 ml of phosphoric acid and then 12.5 g (0.06 mole) of 1,3-dicyclohexylcarbodiimide were added, in turn, to the resulting solution. The reaction mixture was then stirred for 2 hours, after which water was added to it. The reaction mixture was then extracted twice, each time with 200 ml of chloroform. The combined extracts were dried over anhydrous sodium sulfate, and the solvent was then distilled off under reduced pressure. The concentrate was subjected to silica gel column chromatography, and 4.84 g (67%) of 1-benzhydryl-3-oxoazetidine were obtained from the fractions eluted with a 9:1 by volume mixture of toluene and ethyl acetate.

Mass Spectrum (CI, m/e): 238 ($M^+ +1$), 167 [$+CH(phenyl)_2$].

7.26 g (0.03 mole) of 1-benzhydryl-3-oxoazetidine obtained as described above were dissolved in 50 ml of diethyl ether. 60 ml of a 1M tetrahydrofuran solution of methylmagnesium bromide were added to this solution, whilst ice-cooling. The reaction mixture was then stirred for 1 hour, after which 200 ml of water were added to it. The mixture was then extracted with 100 ml of diethyl ether. The organic extract was dried over anhydrous sodium sulfate, and the solvent was distilled off under reduced pressure. The concentrate was subjected to silica gel column chromatography, and 5.92 g (76%) of the title compound were obtained from the fractions eluted with a 3:1 by volume mixture of toluene and ethyl acetate.

Mass Spectrum (CI, m/e): 254 ($M^+ +1$), 167 [$^{30}CH(phenyl)_2$].

Nuclear Magnetic Resonance Spectrum (CDCl$_3$) δ ppm: 1.5 (3H, singlet); 2.15 (1H, broad); 2.97 (2H, doublet, J=8 Hz); 3.2 (2H, doublet, J=8 Hz); 4.35 (1H, singlet); 7.15–1.45 (10H, multiplet).

PREPARATION 5

1-Benzhydryl-3-hydroxypiperidine 5.05 g (0.05 mole) of 3-hydroxypiperidine and 13.82 g (0.1 mole) of potassium carbonate were suspended in 100 ml of dimethylformamide. 12.36 g (0.05 mole) of benzhydryl bromide were then added to the mixture, whilst stirring, and the mixture was stirred for 10 hours at room temperature. At the end of this time, the mixture was poured into 700 ml of water and extracted with ethyl acetate. The extracts were washed with water and dried over anhydrous sodium sulfate. The solvent was then distilled off under reduced pressure. The residue was subjected to silica gel column chromatography, and 10.53 g (yield 78%) of the title compound were obtained as a colorless material from the fractions eluted with a 9:1 by volume mixture of toluene and ethyl acetate.

Infrared Absorption Spectrum (capillary) $\nu_{max}$ cm$^{-1}$: 3340 (—OH).

Mass Spectrum (m/e): 267 ($M^{30}$), 167 [$+CH(phenyl)_2$].

Nuclear Magnetic Resonance Spectrum CDCl$_3$) δ ppm: 1.4–2.5 (9H, multiplet); 3.8 (1H, singlet); 4.3 (1H, singlet); 7.13–7.4 (10H, multiplet).

PREPARATION 6

1-Benzhydryl-3-hydroxpyrrolidine

Following a procedure similar to that described in Preparation 5, except that 4.35 g (0.05 mole) of 3-hydroxypyrrolidine were used instead of the 3-hydroxypiperidine, 10.25 g (yield 81%) of the title compound were obtained.

Infrared Absorption Spectrum (capillary) $\nu_{max}$ cm$^{-1}$: 3360 (—OH).

Mass Spectrum (m/e): 253 (M$^+$), 167 [+CH(phenyl)$_2$].

Nuclear Magnetic Resonance Spectrum (CDCl$_3$) δ ppm: 1.64–2.82 (7H, multiplet); 4.20 (1H, singlet); 4.29 (1H, multiplet); 7.10–7.47 (10H, multiplet).

PREPARATION 7–10

The compounds described below were obtained in a similar manner to that described in Preparation 1.

Preparation 7

1-(4,4'-Difluorobenzhydryl)-3-azetidinyl cyanoacetate

Mass Spectrum (EI, m/e): 342 (M$^+$), 203 [+CH(p-fluorophenyl)$_2$].

Preparation 8

1-Benzhydryl-3-methyl-3-azetidinyl cyanoacetate

Mass Spectrum (CI, m/e): 321 (M$^+$+1), 167 [+CH(phenyl)$_2$].

Preparation 9

1-Benzhydryl-3-pyrrolidinyl cyanoacetate

Mass Spectrum (EI, m/e): 320 (M$^+$), 167 [+CH(phenyl)$_2$].

Preparation 10

1-Benzhydryl-3-piperidyl cyanoacetate

Mass Spectrum (EI, m/e): 334 (M$^+$), 167 (+CH(phenyl)$_2$)

PREPARATIONS 11–14

The compounds described below were obtained in a similar manner to that described in Preparation 2.

Preparation 11

1-(4,4'-Difluorobenzhydryl)-3-azetidinyl amidinoacetate

Mass Spectrum (CI, m/e): 360 (M$^+$+1), 203 [+CH(p-fluorophenyl)$_2$].

Preparation 12

1-Benzhydryl-3-methyl-3-azetidinyl amidinoacetate

Mass Spectrum (CI, m/e): 338 (M$^+$+1), 167 [+CH(phenyl)$_2$].

Preparation 13

1-Benzhydryl-3-pyrrolidinyl amidinoacetate

Mass Spectrum (CI, m/e): 338 (M$^+$+1), 167 [+CH(phenyl)$_2$].

Preparation 14

1-Benzhydryl-3-piperidyl amidinoacetate

Mass Spectrum (CI, m/e): 353 (M$^+$+2), 167 [+CH(phenyl)$_2$].

PREPARATION 15

1-Benzhydryl-3-azetidinyl 2-(3-nitrobenzylidene)acetoacetate 11.95 g (0.05 mole) of 1-benzhydryl-3-hydroxyazetidine and 0.5 ml of triethylamine were dissolved in 50 ml of chloroform 6.3 g (0.075 mole) of diketene were then added dropwise to the solution, after which the reaction mixture was stirred for 10 hours at room temperature, and then water was added to it. The reaction mixture was then stirred for 30 minutes. At the end of this time, the chloroform layer was separated and dried over anhydrous sodium sulfate. The solvent was then distilled off under reduced pressure. The concentrate was subjected to silica gel column chromatography, and 15.07 g (93%) of 1-benzhydryl-3-azetidinyl acetoacetate were obtained, as a pale yellow oil, from the fractions eluted with a 9:1 by volume mixture of toluene and ethyl acetate.

Infrared Absorption Spectrum (capillary) $\delta_{max}$ cm$^{-1}$: 1750 (—CO$_2$—), 1725 (>C=O).

6.46 g (0.02 mole) of 1-benzhydryl-3-azetidinyl acetoacetate obtained as described above, 3.02 g (0.02 mole) of m-nitrobenzaldehyde and 0.29 g (0.002 mole) of piperidinium acetate were dissolved in 10 ml of a 10:1 by volume mixture of toluene and methanol. The reaction mixture was then allowed to stand for 24 hours at room temperature. At the end of this time, ethyl acetate was added to the mixture. The organic layer was separated, washed with water and dried over anhydrous sodium sulfate. The solvent was distilled off under reduced pressure. The concentrate was subjected to silica gel column chromatography, and 3.20 g (yield 35%) of the title compound were obtained, as a pale yellow oil, from the fractions eluted with a 19:1 by volume mixture of toluene and ethyl acetate.

Mass Spectrum (CI, m/e): 457 (M$^+$+1), 167 [+CH(phenyl)$_2$].

Infrared Absorption Spectrum (capillary) $\delta_{max}$ cm$^{-1}$: 1640 (—CO$_2$—).

Nuclear Magnetic Resonance Spectrum (CDCl$_3$) δ ppm: 2.45 (3H, singlet); 3.05 (2H, multiplet); 3.65 (2H, multiplet); 4.35 (1H, singlet); 5.25 (1H, quintet, J=6 Hz); 7.1–8.4 (15H, multiplet).

PREPARATIONS 16+17

The compounds described below were obtained in a similar manner to that described in Preparation 15.

Preparation 16

1-Benzhydryl-3-pyrrolidinyl 2-(3-nitrobenzylidene)acetoacetate

Mass Spectrum (CI, m/e): 471 (M$^+$+1), 167 [+CH(phenyl)$_2$].

Preparation 17

1-Benzhydryl-3-piperidyl 2-(3-nitrobenzylidene)acetoacetate

Mass Spectrum (CI, m/e): 485 (M$^+$+1), 167 [+CH(phenyl)$_2$].

We claim:

1. A compound of formula (I):

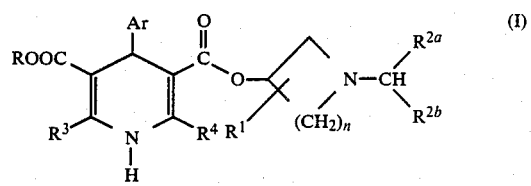

in which:

Ar represents a phenyl group having at least one substituent selected from the group consisting of nitro, $C_1$–$C_4$ haloalkyl, $C_1$–$C_4$ haloalkoxy and cyano groups and halogen atoms;

R represents a $C_1$–$C_{16}$ alkyl group, a $C_3$–$C_6$ cycloalkyl group, a $C_1$–$C_4$ alkyl group having a $C_3$–$C_6$ cycloalkyl substituent, a $C_2$–$C_4$ alkenyl group, a cinnamyl group or a $C_1$–$C_{16}$ alkyl group having at least one substituent selected from the group consisting of hydroxy, $C_1$–$C_4$ alkoxy and $C_1$–$C_4$ alkylthio groups;

R$_1$ represents a hydrogen atom or a $C_1$–$C_3$ alkyl group;

$R^{2a}$ and $R^{2b}$ are independently selected from the group consisting of unsubstituted phenyl groups and substituted phenyl groups having at least one substituent selected from the group consisting of $C_1$–$C_4$ alkyl, $C_1$–$C_4$ alkoxy and $C_1$–$C_4$ haloalkyl groups and halogen atoms;

one of $R^3$ and $R^4$ represents a methyl group and the other represents an amino group; and n is an integer from 1 to 3;

and pharmaceutically acceptable acid addition salts thereof.

2. The compound of claim 1, wherein:

Ar represents a phenyl group having a single substituent selected from the group consisting of nitro, $C_1$–$C_2$ haloalkyl, $C_1$–$C_2$ haloalkoxy and cyano groups or one or two substituents selected from the group consisting of halogen atoms;

R represents a $C_1$–$C_{10}$ alkyl group, a $C_3$–$C_6$ cycloalkyl group, a $C_1$–$C_2$ alkyl group having a $C_3$–$C_6$ cycloalkyl substituent, a $C_3$–$C_4$ alkenyl group, a cinnamyl group or a $C_1$–$C_{10}$ alkyl group having at least one substituent selected from the group consisting of hydroxy, $C_1$–$C_3$ alkoxy and $C_1$–$C_3$ alkylthio groups;

$R^1$ represents a hydrogen atom or a $C_1$–$C_3$ alkyl group;

$R^{2a}$ and $R^{2b}$ are independently selected from the group consisting of unsubstituted phenyl groups and substituted phenyl groups having at least one stubstituent selected from the group consisting of $C_1$–$C_3$ alkyl, $C_1$–$C_3$ alkoxy and trifluoromethyl groups and halogen atoms;

one of $R^3$ and $R^4$ represents a methyl group and the other represents an amino group; and n is an integer from 1 to 3.

3. The compound of claim 2, wherein $R_{2a}$ and $R_{2b}$ are the same.

4. The compound of claim 1, wherein $R^3$ represents a methyl group and $R^4$ represents an amino group.

5. The compound of claim 2, wherein $R^3$ represents a methyl group and $R^4$ represents an amino group.

6. The compound of claim 1, wherein:

Ar represents a phenyl group having a single substituent selected from the group consisting of nitro, trifluoromethyl, difluoromethoxy and cyano groups or having one or two chloro substituents;

R represents a $C_1$–$C_6$ alkyl group, an alkoxyalkyl group containing from three to five carbon atoms, an alkylthioalkyl group containing three or four carbon atoms, a cycloalkyl group containing five or six carbon atoms, a cycloalkylalkyl group containing a total of from four to seven carbon atoms, an alkenyl group containing three or four carbon atoms or a cinnamyl group;

$R^1$ represents a hydrogen atom or a methyl group; and $R^{2a}$ and $R^{2b}$ are the same and each represents a phenyl group or a phenyl group having a single substituent selected from the group consisting of chlorine atoms, fluorine atoms, trifluoromethyl groups, methyl groups and methoxy groups.

7. The compound of claim 6, wherein $R^3$ represents a methyl group and $R^4$ represents an amino group.

8. The compound of claim 1, wherein:

Ar represents a phenyl group having a single substituent selected from the group consisting of nitro, trifluoromethyl, difluoromethoxy and cyano groups or having one or two chloro substituents;

R represents a methyl, ethyl, propyl, isopropyl, butyl, isobutyl, pentyl, hexyl, 2-methoxyethyl, 2-ethoxyethyl, 2-propoxyethyl, 2-methylthioethyl, 3-methylthiopropyl, 2-ethylthioethyl, cyclopentyl, cyclohexyl, cyclopropylmethyl, cyclopentylmethyl, cyclohexylmethyl, allyl, 2-butenyl or cinnamyl group;

$R^1$ represents a hydrogen atom or a methyl group; and $R^{2a}$ and $R^{2b}$ are the same and each represents a phenyl group or a phenyl group having a single substituent selected from the group consisting of chlorine atoms, flourine atoms, trifluoromethyl groups, methyl groups and methoxy groups;

9. The compound of claim 1, wherein:

Ar represents a 2-nitrophenyl group, a 3-nitrophenyl group, a 2-trifluoromethylphenyl group, a 3-trifluoromethylphenyl group, a 2-chlorophenyl group or a 2,3-dichlorophenyl group;

R represents a methyl, ethyl, propyl, isopropyl, butyl, isobutyl, pentyl, hexyl, 2-methoxyethyl, 2-ethoxyethyl, 2-propoxyethyl, 2-methylthioethyl, 3-methylthiopropyl, 2-ethylthioethyl, cyclopentyl, cyclohexyl, cyclopropylmethyl, cyclopentylmethyl, cyclohexylmethyl, allyl, 2-butenyl or cinnamyl group;

$R^1$ represents a hydrogen atom or a methyl group; and $R^{2a}$ and $R^{2b}$ are the same and each represents a phenyl group or a p-fluorophenyl group.

10. The compound of claim 9, wherein $R^3$ represents a methyl group and $R^4$ represents an amino group.

11. The compound of claim 1 selected from the group consisting of :

3-(1benzhydryl-3-azetidinyl) 5-ethyl 2-amino-6-methyl-4-(3-nitrophenyl)-1,4-dihydropyridine-3,5-dicarboxylate;

3-(1-benzhydryl-3-azetidinyl) 5-isopropyl 2-amino-6methyl-4-(3-nitrophenyl)-1,4-dihydropyridine-3,5-dicarboxylate;

3-(1-benzhydryl-3-azetidinyl) 5-cyclohexyl 2-amino-6-methyl-4-(3-nitrophenyl)-1,4-dihydropyridine-3,5-dicarboxylate;

3-(1-benzhydryl-3-azetidinyl) 5-isopropyl 2-amino-4-(2,3-dichlorophenyl)-6-methyl-1,4-dihydropyridine-3,5-dicarboxylate;

3-[1-(4,4'-difluorobenzhydryl)-3-azetidinyl] 5-isopropyl 2-amino-6-methyl-4-(3-nitrophenyl)-1,4-dihydropyridine-3,5-dicarboxylate;

3-(1-benzhydryl-3-methyl-3-azetidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-hexyl 2-amino-6-methyl-4-(3-nitrophenyl)-1,4-dihydropyridine-3,5-dicarboxylate;

3-(1-benzyhydryl-3-piperidyl) 5-isopropyl 2-amino-6-methyl-4-(3-nitrophenyl)-1,4-dihydropyridine-3,5-dicarboxylate;

3-isopropyl 5-(1-benzhydryl-3-azetidinyl) 2-amino-6-methyl-4-(3-nitrophenyl)-1,4-dihydropyridine-3,5-dicarboxylate; and pharmaceutically acceptable acid addition salts thereof.

12. The compound of claim 1 selected from the group consisting of 3-(1-benzhydryl-3-azetidinyl) 5-ispropyl 2-amino-6-methyl-4-(3-nitrophenyl)-1,4-dihydropyridine-3,5-dicarboxylate and pharmaceutically acceptable acid addition salts thereof.

13. The compound of claim 1 selected from the group consisting of 3-(1-benzhydryl-3-azetidinyl) 5-isopropyl 2-amino-4-(2,3-dichlorophenyl)-6-methyl-1,4-dihydropyridine-3,5-dicarboxylate and pharmaceutically acceptable acid addition salts thereof.

14. The compound of claim 1 selected from the group consisting of 3-[1-(4,4'-difluorobenzhydryl)-3-azetidinyl] 5-isopropyl 2-amino-6-methyl-4-(3-nitrophenyl)-1,4-dihydropyridine-3,5-dicarboxylate and pharmaceutically acceptable acid addition salts thereof.

15. A pharmaceutical composition comprising a calcium antagonist amount of an active compound in admixture with a pharmaceutically acceptable carrier or diluent, wherein said active compound is selected from the group consisting of compounds of formula (I):

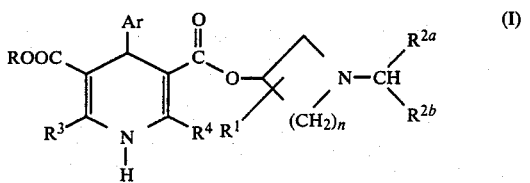

in which:
Ar represents a phenyl group having at least one substituent selected from the group consisting of nitro, $C_1$–$C_4$ haloalkyl, $C_1$–$C_4$ haloalkoxy and cyano groups and halogen atoms;

R represents a $C_1$–$C_{16}$ alkyl group, a $C_3$–$C_6$ cycloalkyl group, a $C_1$–$C_4$ alkyl group having a $C_3$–$C_6$ cycloalkyl substituent, a $C_2$–$C_4$ alkenyl group, a cinnamyl group or a $C_1$–$C_{16}$ alkyl group having at least one substituent selected from the group consisting of hydroxy, $C_1$–$C_4$ alkoxy and $C_1$–$C_4$ alkylthio groups;

$R^1$ represents a hydrogen atom or a $C_1$–$C_3$ alkyl group;

$R^{2a}$ and $R^{2b}$ are independently selected from the group consisting of unsubstituted phenyl groups and substituted phenyl groups having at least one substituent selected from the group consisting of $C_1$–$C_4$ alkyl, $C_1$–$C_4$ alkoxy and $C_1$–$C_4$ haloalkyl groups and halogen atoms;

one of $R^3$ and $R^4$ represents a methyl group and the other represents an amino group; and
n is an integer from 1 to 3;
and pharmaceutically acceptable acid addition salts thereof.

16. The composition of claim 15, wherein:
Ar represents a phenyl group having a single substituent selected from the group consisting of nitro, $C_1$–$C_2$ haloalkyl, $C_1$–$C_2$ haloalkoxy and cyano groups or one or two substituents selected from the group consisting of halogen atoms;

R represents a $C_1$–$C_{10}$ alkyl group, a $C_3$–$C_6$ cycloalkyl group, a $C_1$–$C_2$ alkyl group having a $C_3$–$C_6$ cycloalkyl substituent, a $C_3$–$C_4$ alkenyl group, a cinnamyl group or a $C_1$–$C_{10}$ alkyl group having at least one substituent selected from the group consisting of hydroxy, $C_1$–$C_3$ alkoxy and $C_1$–$C_3$ alkylthio groups;

$R^1$ represents a hydrogen atom or a $C_1$–$C_3$ alkyl group;

$R^{2a}$ and $R^{2b}$ are independently selected from the group consisting of unsubstituted phenyl groups and substituted phenyl groups having at least one substituent selected from the group consisting of $C_1$–$C_3$ alkyl, $C_1$–$C_3$ alkoxy and trifluoromethyl groups and halogen atoms;

one of $R^3$ and $R^4$ represents a methyl group and the other represents an amino group; and
n is an integer from 1 to 3.

17. The composition of claim 16, wherein $R^{2a}$ and $R^{2b}$ are the same.

18. The composition of claim 16, wherein $R^3$ represents a methyl group and $R^4$ represents an amino group.

19. The composition of claim 17, wherein $R^3$ represents a methyl group and $R^4$ represents an amino group.

20. The composition of claim 15, wherein:
Ar represents a phenyl group having a single substituent selected from the group consisting of nitro, trifluoromethyl, difluoromethoxy and cyano groups or having one or two chloro substituents;

R represents a $C_1$–$C_6$ alkyl group, an alkoxyalkyl group containing from three to five carbon atoms, an alkylthioalkyl group containing three or four carbon atoms, a cycloalkyl group containing five or six carbon atoms, a cycloalkylalkyl group containing a total of from four to seven carbon atoms, an alkenyl group containing three or four carbon atoms or a cinnamyl group;

$R^1$ represents a hydrogen atom or a methyl group; and $R^{2a}$ and $R^{2b}$ are the same and each represents a phenyl group or a phenyl group having a single substituent selected from the group consisting of chlorine atoms, fluorine atoms, trifluoromethyl groups, methyl groups and methoxy groups.

21. The composition of claim 15, wherein:
Ar represents a phenyl group having a single substituent selected from the group consisting of nitro, trifluoromethyl, difluoromethoxy and cyano groups or having one or two chloro substituents;

R represents a methyl, ethyl, propyl, isopropyl, butyl, isobutyl, pentyl, hexyl, 2-methoxyethyl, 2-ethoxyethyl, 2-propoxyethyl, 2-methylthioethyl, 3-methylthiopropyl, 2-ethylthioethyl, cyclopentyl, cyclohexyl, cyclopropylmethyl, cyclopentylmethyl, cyclohexylmethyl, allyl, 2-butenyl or cinnamyl group;

$R^1$ represents a hydrogen atom or a methyl group; and $R^{2a}$ and $R^{2b}$ are the same and each represents a phenyl group or a phenyl group having a single substituent selected from the group consisting of chlorine atoms, fluorine atoms, trifluoromethyl groups, methyl groups and methoxy groups.

22. The composition of claim 15, wherein:
Ar represents a 2-nitrophenyl group, a 3-nitrophenyl group, a 2-trifluoromethylphenyl group, a 3-trifluoromethylphenyl group, a 2-chlorophenyl group or a 2,3-dichlorophenyl group;

R represents a methyl, ethyl, propyl, isopropyl, butyl, isobutyl, pentyl, hexyl, 2-methoxyethyl, 2-ethoxyethyl, 2-propoxyethyl, 2-methylthioethyl, 3-methylthiopropyl, 2-ethylthioethyl, cyclopentyl, cyclohexyl, cyclopropylmethyl, cyclopentylmethyl, cyclohexylmethyl, allyl, 2-butenyl or a cinnamyl group;

$R^1$ represents a hydrogen atom or a methyl group; and $R^{2a}$ and $R^{2b}$ are the same and each represents a phenyl group or a p-fluorophenyl group.

23. The composition of claim 15, wherein said active compound is selected from the group consisting of:

3-(1-benzhydryl-3-azetidinyl) 5-ethyl 2-amino-6-methyl-4-(3-nitrophenyl)-1,4-dihydropyridine-3,5-dicarboxylate;

3-(1-benzhydryl-3-azetidinyl) 5-isopropyl 2-amino-6-methyl-4-(3-nitrophenyl)-1,4-dihydropyridine-3,5-dicarboxylate;

3-(1-benzhydryl-3-azetidinyl) 5-cyclohexyl 2-amino-6-methyl-4-(3-nitrophenyl)-1,4-dihydropyridine-3,5-dicarboxylate;

3-(1-benzhydryl-3-azetidinyl) 5-isopropyl 2-amino-4-(2,3-dichlorophenyl)-6-methyl-1,4-dihydropyridine-3,5-dicarboxylate;

3-[1-(4,4'-difluorobenzhydryl)-3-azetidinyl] 5-isopropyl 2-amino-6-methyl-4-(3-nitrophenyl)-1,4-dihydropyridine-3,5-dicarboxylate;

3-(1-benzhydryl-3-methyl-3-azetidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-hexyl 2-amino-6-methyl-4-(3-nitrophenyl)-1,4-dihydropyridine-3,5-dicarboxylate;

3-(2-benzhydryl-3-piperidyl) 5-isopropyl 2-amino-6-methyl-4-(3-nitrophenyl)-1,4-dihydropyridine-3,5-dicarboxylate;

3-isopropyl 5-(1-benzhydryl-3-azetidinyl) 2-amino-6-methyl-4-(3-nitrophenyl)-1,4-dihydropyridine-3,5-dicarboxylate; and pharmaceutically acceptable acid addition salts thereof.

24. A method of treating an animal suffering from a circulatory or coronary disorder by administering thereto a calcium antagonist effective amount of an active compound, wherein the active compound is selected from the group consisting of compounds of formula (I), as defined in claim 1, and pharmaceutically acceptable acid addition salts thereof.

25. The method of claim 24, wherein said active compound is selected from the group consisting of:

3-(1-benzhydryl-3-azetidinyl) 5-ethyl 2-amino-6-methyl-4-(3-nitrophenyl)-1,4-dihydropyridine-3,5-dicarboxylate;

3-(1-benzhydryl-3-azetidinyl) 5-isopropyl 2-amino-6-methyl-4-(3-nitrophenyl)-1,4-dihydropyridine-3,5-dicarboxylate;

3-(1-benzhydryl-3-azetidinyl) 5-cyclohexyl 2-amino-6-methyl-4-(3-nitrophenyl)-1,4-dihydropyridine-3,5-dicarboxylate;

3-(1-benzhydryl-3-azetidinyl) 5-isopropyl 2-amino-4-(2,3-dichlorophenyl)-6-methyl-1,4-dihydropyridine-3,5-dicarboxylate;

3-[1-(4,4'-difluorobenzhydryl)-3-azetidinyl] 5-isopropyl 2-amino-6-methyl-4-(3-nitrophenyl)-1,4-dihydropyridine-3,5-dicarboxylate;

3-(1-benzhydryl-3-methyl-3-azetidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-isopropyl 2-amino-6-methyl-4-(3-nitrophenyl)-1,4-dihydropyridine-3,5-dicarboxylate;

3-(1-benzhydryl-3-pyrrolidinyl) 5-hexyl 2-amino-6-methyl-4-(3-nitrophenyl)-1,4-dihydropyridine-3,5-dicarboxylate;

3-(1-benzhydryl-3-piperidyl) 5-isopropyl 2-amino-6-methyl-4-(3-nitrophenyl)-1,4-dihydropyridine-3,5-dicarboxylate;

3-isopropyl 5-(1-benzhydryl-3-azetidinyl) 2-amino-6-methyl-4-(3-nitrophenyl)-1,4-dihydropyridine-3,5-dicarboxylate; and pharmaceutically acceptable acid addition salts thereof.

* * * * *